United States Patent [19]

Kaplan

[11] 4,361,583
[45] Nov. 30, 1982

[54] ANALGESIC AGENT

[75] Inventor: Jean P. Kaplan, Chevilly Larue, France

[73] Assignee: Synthelabo, Paris, France

[21] Appl. No.: 179,458

[22] Filed: Aug. 19, 1980

[51] Int. Cl.³ .................. A61U 31/165; A61U 31/195
[52] U.S. Cl. ..................................... 424/319; 424/324
[58] Field of Search ............................... 424/324, 319

[56] References Cited

PUBLICATIONS

Chem. Abst. 89-17231(m) (1978).
Chem. Abst. 89-215083(c) (1978).

Primary Examiner—Stanley J. Friedman
Attorney, Agent, or Firm—Wegner & Bretschneider

[57] ABSTRACT

A method of treating pain in a patient through administering to the patient an effective amount of a compound of the formula

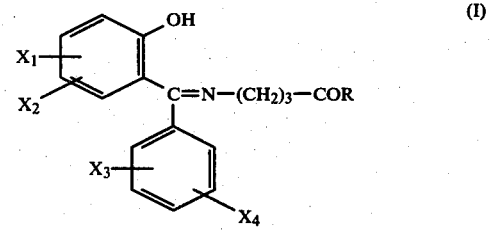

(I)

wherein
$X_1$, $X_2$, $X_3$ and $X_4$ are each, independently, hydrogen, halogen, $NO_2$, $CH_3O$, $CH_3$ or $CF_3$ and
R is OH, ONa or $NH_2$.

4 Claims, No Drawings

ANALGESIC AGENT

The present invention provides a method of treating pain in a patient through administering to the patient an effective amount of a compound of the formula

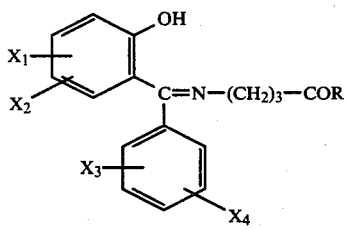

wherein $X_1$, $X_2$, $X_3$ and $X_4$ are each, independently, hydrogen, halogen, $NO_2$, $CH_3O$, $CH_3$ or $CF_3$ and R is OH, ONa or $NH_2$.

In the definition of the compounds (I), $X_1$, $X_2$, $X_3$ and $X_4$ are preferably hydrogen, chlorine or bromine.

Synthesis of the compounds (I) is carried out according to the following scheme

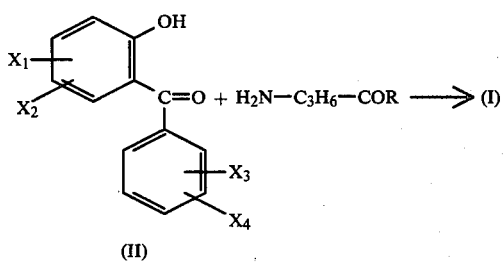

The benzophenone starting materials may be prepared according to the processes describes in the literature, particularly according to U.S. Pat. No. 4,094,992.

The following examples illustrate the invention.

EXAMPLE I

4-[α(4-Chlorophenyl)-5 fluoro-2-hydroxy-benzylidenyl]-amino-butyramide

[$X_1$=5-F, $X_2$=H, $X_3$=4-Cl, R=$NH_2$]

22,3 g (0,1375 mol) of 95% pure carbonyldiimidazole are added in portions, over the course of 10 minutes, to a solution, stirred at 0°, of 42 g (0,125 mol) of 4-[α-(4-chlorophenyl)-5 fluoro-2-hydroxy-benzylidenyl]-amino-butyric acid in 130 ml of anhydrous THF, and the mixture is stirred in the cold for 15 minutes and then at ambient temperature for 15 minutes. The solution obtained is added dropwise, whilst stirring, to 800 ml of liquid ammonia and the mixture is stirred until evaporation is complete.

The oily residue is taken up in 500 ml of chloroform and the solution is washed with water, an aqueous bicarbonate solution and again with water. It is dried over $MgSO_4$ in the presence of vegetable chacoal and filtered, and the filtrate is evaporated to dryness. An oil is obtained, which crystallises by trituration in petroleum ether. The product is washed with petroleum ether and suction-drained to the maximum extent. It is recrystalised from a 1:1 mixture of cyclohexane and toluene, with treatment with vegetable charcoal, and is dried in a heated vacuum desicator at 60°. Weight obtained: 28 g; yield: 67%; melting point=133°-135° C. (Tottoli).

Analysis Calculated %: C 60.99: H 4,82: N 8,37: Cl 10,59: F 5,67: Found %: C 60,91: H 4,83: N 8,36: Cl 10,84: F 5,74: C 60.97: H 4,78: N 8,26: Cl 10,73: F 5,76.

EXAMPLE II

The compounds (I) of the method of the invention have been demonstrated to be analgesic agents. This activity has been tested by the acetic acid writhing test in the mouse (reference: R. KOSTER, M. ANDERSON & E. J. de BEER, Fred. Proc., 1959, 18, 412.

The substances (I) are administered in several doses (50 and 200 mg/kg) per os 60 minutes before the test.

The percentage of decrease of writhing is measured, compared with controls: for the compounds (I) at the dose of 50 mg/kg the percentage is from 20 to 40; at the dose of 200 mg/kg the percentage is from 60 to 80. The $ED_{50}$ is from 90 to 110 mg/kg p.o. The LD 50 toxicity (50% lethal dose) was determined on CD1 mice, per os. The LD 50 is from 800 to 4000 mg/kg.

These results show that the compounds (I) of the method of the invention are analgesic agents suitable for the treatment of pain. The compounds (I) are advantageously combined with a compatible carrier so that they can be administered orally or parenterally. For oral administration, any conventional pharmaceutical form may be used, that is to say tablets, dragees, gelatine-coated pills, capsules, cachets and drinkable solutions or suspensions.

The daily dose of the compound (I) is from about 50 to about 2500 mg.

We claim:

1. A method of treating pain which comprises administering to a patient suffering from pain an effective dosage of a compound (I) to relieve said pain, said compound (I) having the formula

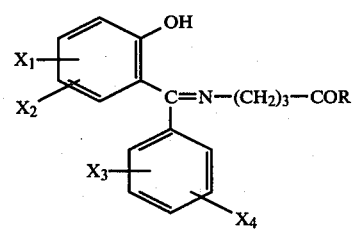

wherein $X_1$, $X_2$, $X_3$ and $X_4$ are each, independently, hydrogen, halogen, $NO_2$, $CH_3O$, $CH_3$ or $CF_3$ and R is OH, ONa or $NH_2$.

2. A method of claim 1, wherein said compound (I) is 4-[α(4-chlorophenyl) 5-fluoro-2-hydroxy-benzylidenyl]-amino-butyramide.

3. A method of claim 1, wherein said compound (I) is 4-[α(4-chlorophenyl) 5-fluoro-2-hydroxy-benzylidenyl]-amino-butyric acid.

4. A method of claim 1, wherein said compound (I) is 4-[α(2-bromo-phenyl) 5-chloro-2-hydroxy-benzylidenyl]-amino-butyramide.

* * * * *